United States Patent [19]

Gouw

[11] 4,395,903

[45] Aug. 2, 1983

[54] APPARATUS AND METHOD FOR DETERMINING THE VAPOR PRESSURE OF HEAVY HYDROCARBON MIXTURES

[75] Inventor: T. H. Gouw, El Cerrito, Calif.

[73] Assignee: Chevron Research Company, San Francisco, Calif.

[21] Appl. No.: 292,279

[22] Filed: Aug. 12, 1981

[51] Int. Cl.³ .............................................. G01N 7/16
[52] U.S. Cl. ...................................................... 73/64.2
[58] Field of Search ....................... 73/64.2, 61.3, 23.1; 374/54; 364/558, 556

[56] References Cited

FOREIGN PATENT DOCUMENTS 1243900  7/1967  Fed. Rep. of Germany ....... 73/64.2
2153472  5/1973  Fed. Rep. of Germany ....... 73/61.3
1154078  10/1957  France .................................. 73/64.2

Primary Examiner—E. R. Kazenske
Assistant Examiner—Joseph W. Roskos
Attorney, Agent, or Firm—Burns, Doane, Swecker & Mathis

[57]  ABSTRACT

A vapor pressure method and apparatus for accurately determining the vapor pressure of heavy crude oil and residual fractions is disclosed. A test sample of the crude or residuum is held in a constant temperature vessel from which vapors are continuously withdrawn and recycled into the crude or residuum until equilibrium is established. Once equilibrium is established a specimen of the vapors is extracted from the recycle line and analyzed by a gas chromatograph. Vapor pressure is calculated from the chromatographic analysis by known procedures.

8 Claims, 3 Drawing Figures

FIG.__1.

APPARATUS AND METHOD FOR DETERMINING THE VAPOR PRESSURE OF HEAVY HYDROCARBON MIXTURES

BACKGROUND OF THE INVENTION

1. Field of the Invention

The invention relates to an apparatus and method for determining the vapor pressure of heavy hydrocarbon stocks such as heavy crude oil and residual fractions.

2. Description of the Prior Art

Vapor pressure specifications are used in oil processing for quality control purposes and for monitoring compliance with safety and regulatory regulations. For instance, air pollution control regulations specify maximum permissible vapor pressures in oil storage tanks. Accordingly, there is a continuing need to determine the vapor pressures of hydrocarbon stocks such as crude oils from petroleum, shale, coal, tar sands and other sources and fractions of such oils.

Many vapor pressure tests are suitable for determining the vapor pressure of low boiling stocks such as gasoline and light distillates. When used on heavy stocks, however, these tests typically give erroneous measurements due to the presence of dissolved air or traces of moisture or the inability to accurately determine the contribution of small amounts of light components. For instance, the Reid vapor pressure test (ASTM D-323-79) is not sensitive enough for use with heavy crude oils and residual stocks. When used on such heavy stocks a substantial portion of the observed pressure is attributable to dissolved air and traces of moisture. Other manometric techniques, such as the isoteniscope test (ASTM D-2879-75), also give erroneous readings with heavy stocks due to the presence of dissolved air.

Various dynamic methods for measuring vapor pressure are described in the *Encyclopedia of Chemical Technology*, Kirk-Othmer 2nd Ed., Vol. 21 pp 230–238 (1970). Most of the described methods involve vapor-liquid equilibrium stills. Jentoft et al, *Rapid Determination of the Vapor Pressure of Lubricating Oils and Hydraulic Fluids,* Anal. Chem. 40, 1014 (1968) describes a dynamic vapor pressure technique that is designed to determine the bulk vapor pressure of a liquid and to ignore the effect of traces of light components. It is, however, not appropriate for determining the vapor pressure of heavy stocks because it ignores the contribution of light components.

It is also known that the vapor pressure of petroleum fractions can be determined using gas chromatographic analysis. In Eggertsen F. T., et al, *Estimation of the Vapor Pressure of Petroleum Distillate Fractions from Gas Chromatographic Data,* Anal. Chem. 52, 2069-2072 (1980), a sample of the fraction is analyzed chromatographically to develop a chromatogram. The chromatogram is compared to chromatograms of standard compounds of known carbon content and is divided into areas by carbon number. The area of each carbon number segment on the chromatogram is determined and the mol fractions of the components are calculated from the areas. Partial pressures are obtained by multiplying the mol fraction by the saturation pressure determined using the Antoine equation. The vapor pressure is calculated by summation of the partial pressures.

Application of the above described gas chromatograph technique to measuring the vapor pressure of a heavy crude or residual fraction poses two problems. Firstly, with such stocks elution from the chromatograph is incomplete, thus making it impossible to calculate the mol fractions of the lighter components from the chromatogram. Secondly, the analysis is based on the liquid phase. Therefore, to calculate the corresponding vapor pressure the fugacities for each component of the liquid sample must be known. They are typically not known and fugacities must be assumed on the basis that there are no azeotropes present between the components of the sample.

A principal object of the present invention is to provide an apparatus and method for determining the vapor pressure of heavy hydrocarbon stocks accurately with relative ease and simplicity.

SUMMARY OF THE INVENTION

One aspect of the invention is a method for determining the vapor pressure of a heavy liquid hydrocarbon mixture comprising:

(a) maintaining the liquid hydrocarbon mixture at a substantially constant temperature in a closed vessel with a vapor space above the liquid;

(b) continuously withdrawing vapors from said vapor space;

(c) recycling the withdrawn vapors into the liquid hydrocarbon mixture below the liquid-vapor interface for a time sufficient to establish equilibrium between the liquid and vapor in the vessel;

(d) thereafter analyzing the composition of said withdrawn vapors by gas chromatography;

(e) calculating the partial pressures of the components of said vapors from the chromatographic analysis; and (f) calculating the vapor pressure of the mixture by summing the partial pressures of the components.

A second aspect of the invention is an apparatus for determining the vapor pressure of a heavy liquid hydrocarbon mixture comprising in combination:

(a) a closed vessel in which the liquid hydrocarbon mixture is maintained with a vapor space above the liquid mixture;

(b) means for maintaining the temperature within the vessel substantially constant;

(c) a conduit for continuously withdrawing vapors from the vessel and recycling them back to the vessel at a location below the liquid-vapor interface, one end of the conduit opening into the vapor space and the other end opening into the liquid mixture;

(d) a pump connected into the conduit between said ends for providing the driving force for withdrawing the vapors from the vessel and recycling them back to the vessel;

(e) a vapor sampling means connected to the conduit between said ends for withdrawing a sample of the vapors from the lumen of the conduit once equilibrium has been established between the liquid and vapors within the vessel;

(f) sample analyzing means connected to the vapor sampling means for quantitatively analyzing the composition of the sample; and (g) computer means connected to the sample analyzing means for calculating the partial pressures of the components of the composition from the analysis of the composition and summing the partial pressures to obtain the vapor pressure of the liquid hydrocarbon mixture.

DETAILED DESCRIPTION OF THE INVENTION

As used herein the term "heavy liquid hydrocarbon mixture" means hydrocarbon stocks derived from petroleum or other oil sources, a substantial portion of the components of which boil above about 650° F.

Figure 1:
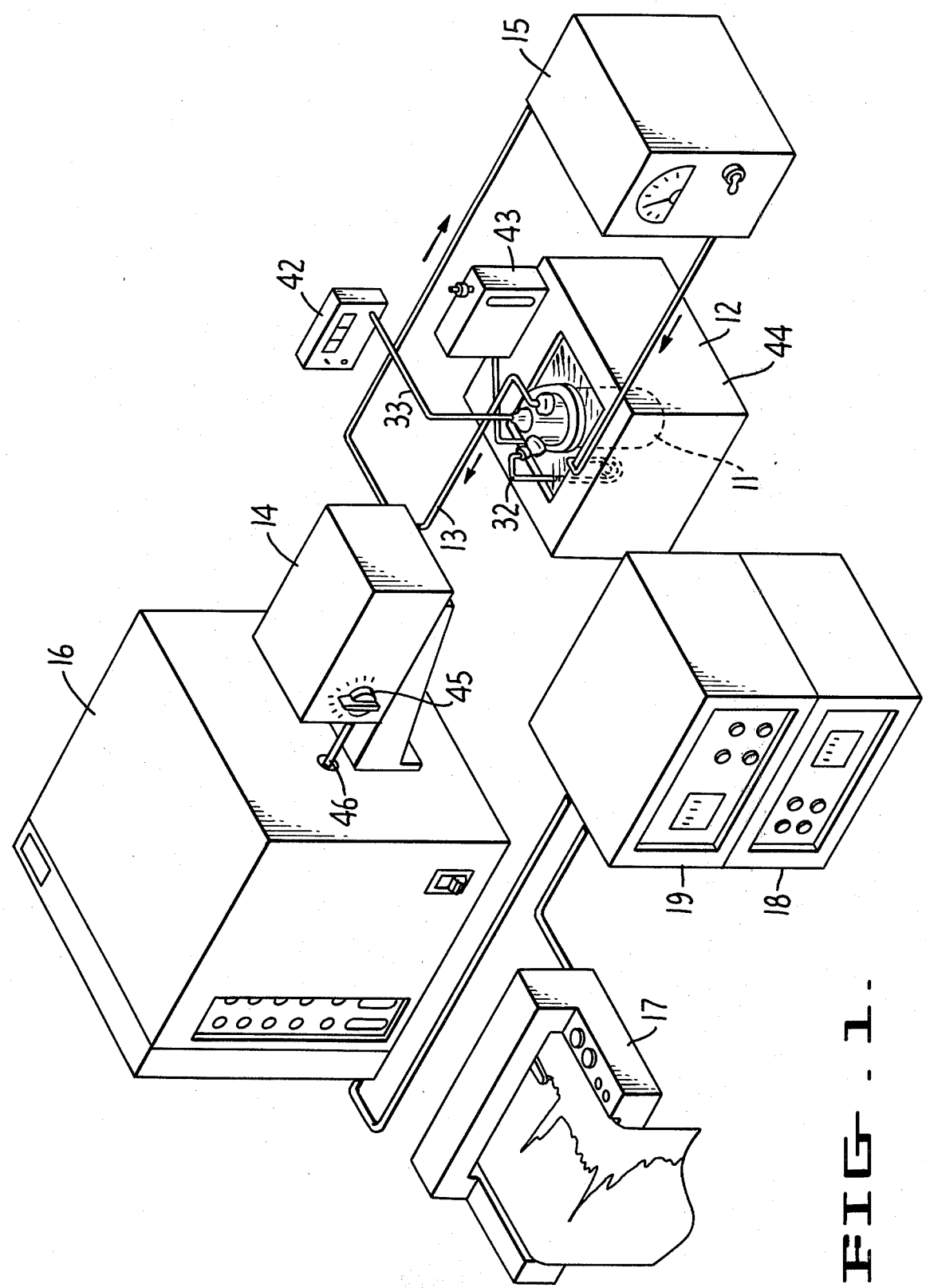
FIG. 1 is a perspective view of the preferred embodiment of the vapor pressure apparatus of the invention.

FIG. 1 is an overall view of the pieces of equipment that are used to measure vapor pressure in accordance with the invention. The equipment shown in FIG. 1 includes: a vapor pressure vessel 11; a constant temperature liquid bath 12 in which the vapor pressure vessel is partly immersed; a vapor collector-recycle tube 13; a heated sampling valve 14 connected into the collector recycle tube; a heated gas recirculating pump 15; a gas chromatograph 16 connected to the sampling valve; a chart recorder 17 connected to the chromatograph for making a graphic record of the chromatograph output; a temperature programmer 18 for regulating the temperature of the chromatograph; and an electronic integrator - computer system 19 for determining the areas of the chromatographic peaks and for calculating vapor pressure from the chromatographic analysis.

Figure 2:
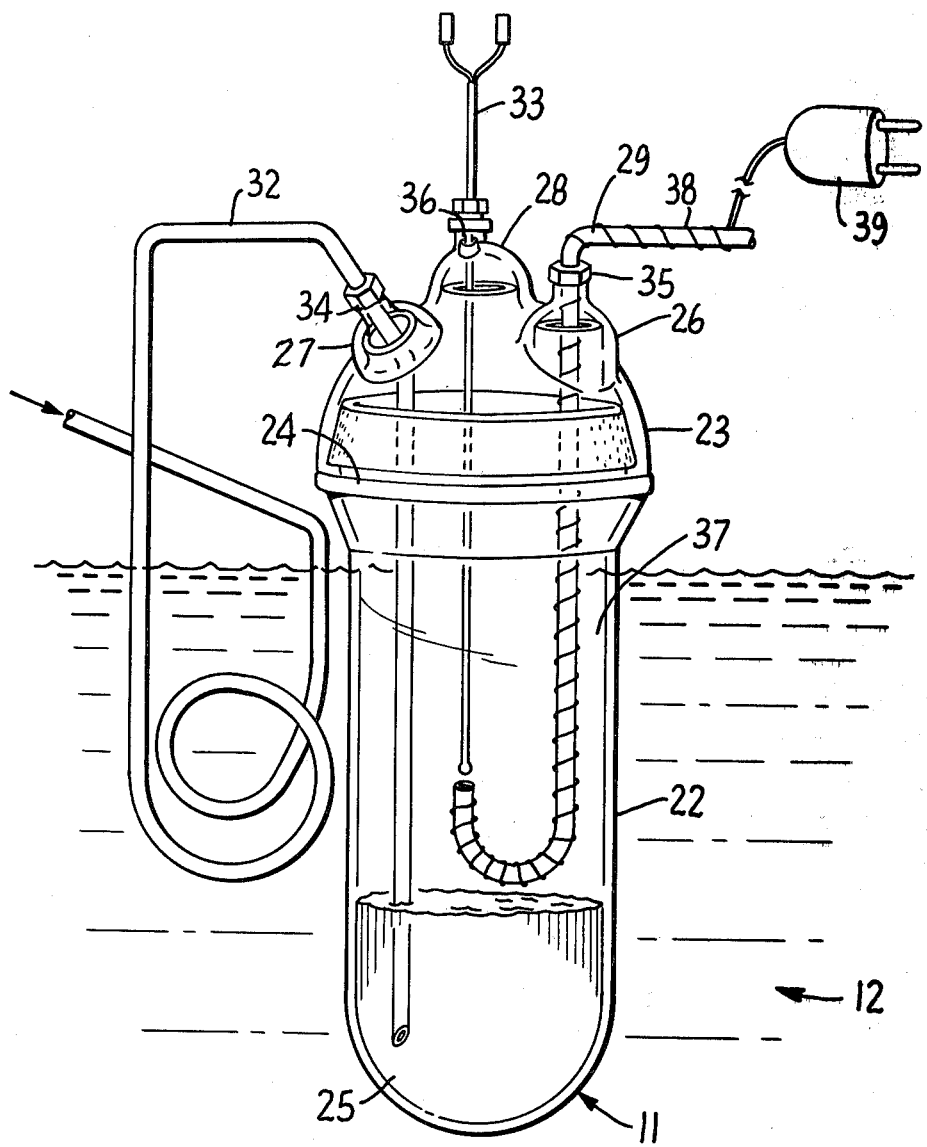
FIG. 2 is an elevational view of the vapor pressure vessel of the apparatus of FIG. 1.

The vapor pressure vessel 11 is shown in detail in FIG. 2. The vessel comprises an open-ended generally cylindrical main body 22 and a lid or cap 23. The vessel lid makes a fluid-tight fit with the upper lip of the main body by means of an O-ring 24, thereby closing the vessel. A sample of liquid hydrocarbon mixture 25 is contained in the bottom of the vessel. The lid of the vessel has a trio of bubble caps 26, 27, 28 through which are received, respectively, a vapor withdrawl segment 29 of tubing 13, a vapor return segment 32 of tubing 13, and a thermocouple 33. The openings of caps 26, 27, and 28 are fitted with Gyrolock interchangeable fitting 34, 35, and 36 that form fluid-tight seals about the segments of tubing and thermocouple to prevent leakage of vapors from the vessel. The end of the vapor withdrawal segment of the tubing is bent upwardly and opens into the vapor space 37 above the liquid. An electrical heating coil 38 is wrapped about a portion of the vapor withdrawal segment of tubing for heating the withdrawn vapors to prevent them from condensing within the tubing. The ends of the coil are connected to plug 39 that may be inserted in an electrical outlet (not shown). The end of the thermocouple is positioned directly above the opening of segment 29 so that the temperature of the vapors withdrawn from the vapor space may be determined. The thermocouple is connected to a calibrated voltmeter or digital temperature indicator 42 from which that temperature may be read.

The vapor return segment of the tubing extends from cap 27 down through the vessel and opens below the liquid-vapor interface. Before entering the vessel the return segment is coiled below the fluid level within bath 12 to insure that the return vapors enter the vessel at substantially the same temperature as the vessel's contents. As shown in FIGS. 1 and 2, a substantial portion of the main body of the vessel is immersed in the fluid of the bath. That fluid, which is typically water, is maintained at a substantially constant temperature by a bath temperature regulating means, such as a thermoregulator 43 connected to an electrical heating coil, (not shown) contained within the housing 44 of the bath. The bath housing will usually be insulated to further facilitate the maintenance of a constant temperature.

Vapors are continuously withdrawn from the vapor space above the liquid in the vessel via segment 29 of tubing 13 by the suction created in that segment by pump 15. The movement of vapors through tubing 13 is indicated schematically in FIG. 1 by arrows. These vapors are carried from the vessel by tubing 13 to a heated sampling valve mechanism 14. Mechanism 14 is basically a 6 port valve that permits a sample of the vapors passing through the tubing to be extracted for analysis. Except when the sample is taken this valve is normally positioned so that the vapors flow through valve and pass directly to the suction side of pump 15. Valve mechanism 14 is operated manually by a control knob 45. The vapors are pressurized as they pass through the pump and are exhausted into segment 32 of the tubing. They are carried by the segment through the bath and then injected into the vessel below the liquid-vapor interface. Such continuous withdrawal and recycle of vapors establishes vapor-liquid equilibrium at the temperature of the liquid sample. Equilibrium will normally be established within about ten minutes after the bath temperature has been established and vapor circulation is initiated. Once equilibrium has been established valve mechanism 14 is actuated manually to extract a sample of the vapors passing through the tubing. The volume of the sample is fixed by the size of the sample loop in the valve and will usually be about 0.1 to 1.0 ml. After the sample is taken the valve is returned to its normal position. The sample is carried from mechanism 14 into the gas chromatograph by line 46.

The chromatograph and the analysis conditions should be such that a good separation and quantitation of the light components ($C_6$ and below) of the sample occurs. In addition, it is desirable to elute the heavier components of the sample from the chromatograph column in a reasonable length of time. The separation is, therefore, desirably carried out by temperature programming the column with programmer 18. Such chromatographs and temperature programmers are well known, commercially available equipment. Their structure and operation do not, therefore, require description herein.

The chromatograms produced by the chromatograph and chart recorder may be analyzed by the methods described by Eggertsen et al, *Estimation of the Vapor Pressure of Petroleum Distilled Fractions from Gas Chromatographic Data*, supra. In the apparatus shown in FIG. 1 the integrations and calculations involved in that analysis are made by the electronic integrator - computer system 19.

In operation the chromatograph apparatus is first calibrated with a pure reference hydrocarbon whose vapor pressure is known. The vapor pressure of a pure compound is only a function of the temperature. The relation between the vapor pressure, $P_r$, and the temperature, $T_1$, is given by the Clausius-Clapeyron equation;

$$\text{Log } P_r = C_1 + C_2/(T_1 + C_3) \qquad (1)$$

where $C_1$, $C_2$, and $C_3$ are constants and $T_1$ is the temperature is ° C.

If $P_r$ is expressed in mm Hg, the weight of the molecules of this compound in 1 ml of vapor above the liquid equals $W_r$, where:

$$W_r = 1 \cdot P_r/760 \cdot M_r/22414 \cdot 273.13/(273.13+T_1) \tag{2}$$

where $M_r$ is the molecular weight of the reference compound.

Equation 2 is valid irrespective of the total pressure of the system, P, as long as:

$$P \geq P_r$$

If P equals $P_r$, the product will boil. If $P<P_r$, then no equilibrium can take place since a net mass transport of molecules from the liquid into the vapor space occurs under such conditions.

In the present invention $P>P_r$ and the number of molecules per unit volume is hence fixed by the temperature of the bath only.

As the gas is swept away from the liquid surface into the hot conduit leading into the chromatograph, the gas will not be in contact with the liquid anymore and it will expand. The pressure in the sampling loop of the gas chromatograph will be assumed to be equal to the pressure in the reference cell—strictly speaking there is, of course, a small pressure drop over the tube because of the flow of gas. At these low pressures, one can assume the ideal gas laws to hold and the weight of reference molecules per unit volume will hence change into $W'_r$, where:

$$W'_r = W_r(273.13+T_1)/(273.13+T_s) \tag{3}$$

where $T_s$ is the temperature of the sample loop. If one injects this sample in the gas chromatograph, one will get a peak with an area $A_r$, which is related to the previous parameters by:

$$A_r = R_r L W'_r \tag{4}$$

where $R_r$ is the response factor (cm² peak area/g sample injected) and L is the volume of the sample (or the sample loop in the chromatograph in the embodiment of the drawings). Combination of Equations 2, 3, and 4 yields:

$$A_r = R_r L \ P_r/760 \cdot M_r/22414 \cdot 273.13/(273.13+T_s) \tag{5}$$

For a sample of a heavy liquid hydrocarbon mixture heated to a temperature $T_2$, the same analysis as above may be used for any hydrocarbon component in the vapor space. In the range we are considering, the total number of hydrocarbon molecules in a unit space is only dependent on the temperature and since the sample is a mixture, on the vapor/liquid ratio. But again, as in the case of the pure compound, there should be no pressure dependence.

Hence, the amount of component X in 1 ml of vapor in equilibrium with the liquid is also:

$$W_x = 1 \cdot P_x/760 \cdot M_x/22414 \cdot 273.13/(273.13+T_2) \tag{6}$$

Expansion does take place as the sample travels from the liquid surface to the gas sampling loop; and a similar expression as that given in Equation 5 covers this phenomenon, i.e., $$A_x = R_x L \ P_x/760 \cdot M_x/22414 \cdot 273.13/(273.13+T_s) \tag{7}$$

Combining Equations 5 and 7 yield:

$$P_x = P_r R_r/R_x \cdot A_x/A_r \cdot M_r/M_x$$

The ratio $R_r/R_x$ may be obtained from the response factor tables for the particular gas chromatography system used. The values of $P_r$, $M_r$ and $A_r$ are known. The value of $A_x$ is calculated from the chromatogram for the heavy hydrocarbon mixture and the value of $M_x$ is estimated based on the carbon number ascribed to the hydrocarbon X, based on the location of its peak on the chromatogram. Partial pressures for the various components of the heavy hydrocarbon mixture are thus determined. These partial pressures are summed to obtain the vapor pressure of the mixture. To obtain a totally accurate vapor pressure, a complete component analysis of the vapors is required. As a practical matter, however, it is usually adequate to have a good resolution of the lighter components only. The $C_7$ and heavier components may be lumped together by carbon number. Their contribution to the vapor pressure is relatively small, and the small differences in their molecular weights will not have a significant effect on the accuracy of the determination.

The following examples illustrate the apparatus and method of the invention. These examples are not intended to limit the invention in any manner.

EXAMPLE 1

An apparatus essentially identical to that shown in FIG. 1 was used to determine the vapor pressure of a heavy crude petroleum oil, identified as Midway Sunset crude, at 35° C., 65° C. and 85° C. The approximate volume of the vapor pressure vessel was 500 ml. A 100 ml portion of the crude was charged to the vessel in each test. The volume ratio of vapor space-to-liquid was, therefore, about 4:1. The pressure of the vapor space was atmospheric pressure. The withdrawn vapors were heated at least 100° C. higher than the bath temperature to avoid condensation. The volume of each vapor sample injected to the chromatograph was 0.1 ml. An HP 5750 gas chromatograph equipped with flame ionization detectors was used. The sample was fractionated on a 20 ft and ⅛ inch steel column packed with 3% by weight silicon (OV-101) on 80-100 mesh (standard Tyler screen) Chromosorb W HP adsorbent. The elutions were temperature programmed from 70°-225° C. at 10° C./minute. n-Dodecane was used to calibrate the system.

Figure 3:
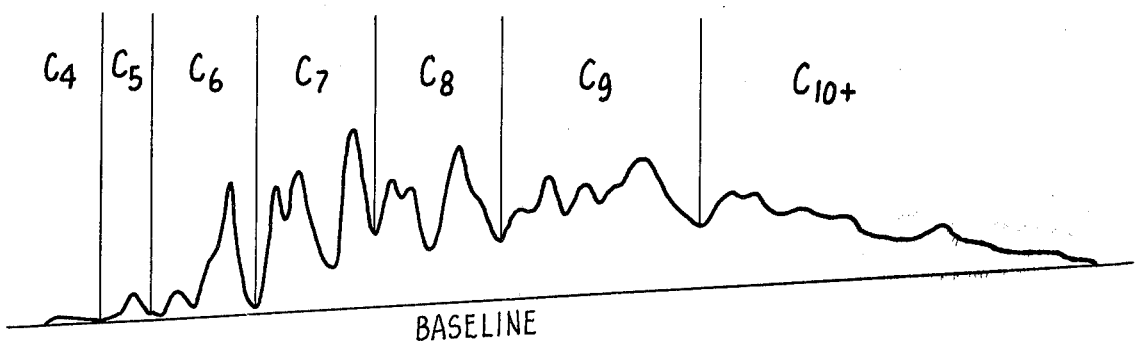
FIG. 3 is a chromatogram showing an analysis of vapors made using the invention apparatus.

FIG. 3 is a reproduction of the chromatogram obtained. The chromatogram was divided by carbon number by comparison with chromatograms of pure reference hydrocarbons. The areas under the C-number peaks were integrated with a Columbia Scientific Industries model CSI-208 automatic integrator and the partial pressures of the components were calculated from those areas as above. The partial pressures were summed to obtain the vapor pressures of the crude at the various test temperatures. These vapor pressures are reported in the table below.

EXAMPLE 2

The vapor pressure of another crude petroleum oil, identified as East Coalinga crude was determined at 32° C., 38° C., and 60° C. using the apparatus and method described in Example 1. These vapor pressures are also reported in the table below.

| Sample Identification | Equilibrium Temp. °C. | Vapor Pressure mmHg |
|---|---|---|
| Midway Sunset | 35 | 1.17 |
| | 65 | 3.20 |
| | 85 | 7.08 |
| East Coalinga | 32 | 4.28 |
| | 38 | 4.92 |
| | 60 | 13.87 |

Plots of the log of the vapor pressure versus the reciprocal of the equilibrium temperature in °K. gave linear relationships between log P and 1/T for the samples of Examples 1 and 2. By linear regression the following relationships between vapor pressure and temperature for the two crude oils were calculated:

Midway Sunset $-\log P = 3.57 \cdot 10^{-3} - 5.01 \cdot 10^{31}\ 4/T$

East Coalinga $-\log P = 3.25 \cdot 10^{-3} - 5.414 \cdot 10^{-4}/T$ where P is the vapor pressure in mm Hg and T is the temperature in °K.

As illustrated by these examples the invention enables accurate vapor pressure measurement of heavy stocks by analyzing a truly equilibrium vapor phase rather than a liquid phase. Sample handling in the method is minimal and no corrections are required for the heavy stock or for the fugacities of the volatile components.

Modifications of the above described embodiments and examples of the invention apparatus and process that are obvious to persons of ordinary skill in physical chemistry and the analytical methods and apparatus arts are intended to be within the scope of the following claims.

I claim:

1. Method for determining the vapor pressure of a heavy liquid hydrocarbon mixture comprising:
   (a) maintaining the liquid hydrocarbon mixture at a substantially constant temperature in a closed vessel with a vapor space above the liquid;
   (b) continuously withdrawing vapors from said vapor space;
   (c) recycling the withdrawn vapors into the liquid hydrocarbon mixture below the liquid-vapor interface for a time sufficient to establish equilibrium between the liquid and vapor in the vessel;
   (d) thereafter analyzing the composition of said withdrawn vapors by gas chromatography;
   (e) calculating the partial pressures of the components of said vapors from the chromatographic analysis; and
   (f) calculating the vapor pressure of the mixture by summing the partial pressures of the components.

2. The method of claim 1 wherein a sample of the withdrawn recycling vapors is taken after step (c) and said sample is used for analysis of step (d).

3. The method of claim 1 or 2 wherein the vapors are heated after they are withdrawn from the vessel to prevent them from condensing during recycle and are cooled to said temperature substantially immediately before being introduced into the liquid hydrocarbon mixture 4. The method of claim 1 wherein said time is at least about 10 minutes.

5. Apparatus for determining the vapor pressure of a heavy liquid hydrocarbon mixture comprising in combination:
   (a) a closed vessel in which the liquid hydrocarbon mixture is maintained with a vapor space above the liquid mixture;
   (b) means for maintaining the temperature within the vessel substantially constant;
   (c) a conduit for continuously withdrawing vapors from the vessel and recycling them back to the vessel at a location below the liquid-vapor interface, one end of the conduit opening into the vapor space and the other end opening into the liquid mixture;
   (d) a pump connected into the conduit between said ends for providing the driving force for withdrawing the vapors from the vessel and recycling them back to the vessel;
   (e) a vapor sampling means connected to the conduit between said ends for withdrawing a sample of the vapors from the lumen of the conduit once equilibrium has been established between the liquid and vapors within the vessel;
   (f) sample analyzing means connected to the vapor sampling means for quantitatively analyzing the composition of the sample; and
   (g) computer means connected to the sample analyzing means for calculating the partial pressures of the components of the composition from the analysis of the composition and summing the partial pressures to obtain the vapor pressure of the liquid hydrocarbon mixture.

6. The apparatus of claim 5 wherein said means for maintaining the temperature within the vessel substantially constant is a substantially constant temperature liquid bath in which the vessel is immersed.

7. The apparatus of claim 5 wherein the sample analyzing means is a gas chromatograph, capable of temperature programmed operation.

8. The apparatus of claim 5 including heating means connected to the segment of said conduit proximate said one end for heating the withdrawn vapors to prevent them from condensing during recycle and wherein the segment of said conduit proximate said other end communicates with said temperature maintaining means whereby the vapors are cooled to substantially said temperature before they are introduced into the liquid hydrocarbon mixture within the vessel.

* * * * *